United States Patent [19]

Hadary

[11] Patent Number: 4,520,833

[45] Date of Patent: Jun. 4, 1985

[54] TOOTHPICK HOLDER

[76] Inventor: Joseph Hadary, 5405 Linden Ct., Bethesda, Md. 20814

[21] Appl. No.: 476,555

[22] Filed: Mar. 16, 1983

[51] Int. Cl.³ ............................................. A61C 15/00
[52] U.S. Cl. ...................................................... 132/90
[58] Field of Search ................ 132/89, 90, 91, 92-93; 433/147; 206/380

[56] References Cited

U.S. PATENT DOCUMENTS

| | | | |
|---|---|---|---|
| 2,981,264 | 4/1961 | De Felice | 132/91 |
| 3,106,216 | 10/1963 | Kirby | 132/92.2 |
| 4,041,962 | 8/1977 | Johansson | 132/91 |

Primary Examiner—Gregory E. McNeill
Attorney, Agent, or Firm—Dennis H. Lambert

[57] ABSTRACT

A toothpick holder with a plurality of toothpick-gripping openings oriented to hold toothpicks in different positions to facilitate access to different portions of the teeth. The holder is generally T-shaped, with an elongate handle having a cross-piece at one end. The cross-piece has oppositely oriented openings in its opposite ends for selectively holding first one toothpick and then another such that the toothpicks are properly oriented to gain access to different areas of the teeth. Each opening is larger on one side of the cross-piece than on the other, having a stepped or reduced portion between the ends of the openings, defining a shoulder. As a toothpick is inserted through the opening, the narrow edge of the toothpick engages the shoulder and a portion of the narrow edge of the toothpick is shaved off or rolled back, tending to wedge the toothpick in place.

5 Claims, 8 Drawing Figures

TOOTHPICK HOLDER

BACKGROUND OF THE INVENTION

1. Field of the Invention

This invention relates to dental implements, and more particularly, to a toothpick holder for holding toothpicks in a plurality of orientations for facilitating access to different areas of the mouth.

2. Prior Art

Proper and frequent cleaning of the teeth is necessary for maintaining oral hygiene and healthy teeth and gums. While brushing is the most common method of cleaning teeth, it is not entirely satisfactory and the dental profession recommends other methods of cleaning as well, such as flossing. Moreover, the proper use of toothpicks is beneficial in any oral hygiene program, particularly for cleaning between the teeth.

However, except for a few attempts at developing a toothpick holder, people are generally limited to the use of toothpicks held in the user's hand. Accordingly, the use of a toothpick is only partially effective in cleaning the teeth, and those areas which are difficult to reach are usually not cleaned.

Examples of prior art toothpick holders are shown in U.S. Pat. Nos. 710,498, 1,291,282 and 3,892,040. In U.S. Pat. No. 710,498 a quill-like member is curved to form a pick. U.S. Pat. No. 1,291,282 discloses a threaded holder having a pair of openings therein for receiving a toothpick in either of two different positions. U.S. Pat. No. 3,892,040 discloses a holder having a threaded sleeve which is movable against a round toothpick to clamp the toothpick in position.

None of the devices described in the above patents comprises a holder for holding a toothpick with a wedge-shaped cross-section in a particular orientation at the opposite ends of a T-shaped handle or holder for properly orienting the wedge-shaped toothpick for access to different areas of the teeth at different sides of the mouth.

SUMMARY OF THE INVENTION

It is, therefore, a primary object of this invention to provide a toothpick holder which is economical and simple in construction and which securely holds toothpicks in a plurality of orientations to facilitate access to different areas of the teeth.

Another object of the invention is to provide a toothpick holder which is of essentially one-piece construction and which has a plurality off shaped openings at one end of a handle for holding first one toothpick and then another in different predetermined orientations.

A more specific object of the invention is to provide a toothpick holder for holding a toothpick having a wedge-shaped cross-section such that a toothpick may be inserted into one of a plurality of shaped openings, with the toothpick being properly oriented for one side of the mouth or the other, depending upon which opening the toothpick is inserted into.

These and other objects of the invention are accomplished by a toothpick holder having a generally T-shaped configuration comprising an elongate handle with a cross-piece at one end, and in which shaped openings are formed in opposite ends of the cross-piece for holding first one and then another toothpick to facilitate access to the teeth at different sides of the mouth, depending upon which opening the toothpick is inserted into. The holder is of one-piece construction and provides in one implement, without the necessity of manipulating clamps, adjustments, etc., a simple and inexpensive tool for holding toothpicks in a plurality of orientations.

BRIEF DESCRIPTION OF THE DRAWINGS

Other objects of this invention will appear in the following description and appended claims, reference being made to the accompanying drawings forming a part of the specification, and wherein like reference numerals designate like parts throughout the several views.

DESCRIPTION OF THE PREFERRED EMBODIMENTS

Figure 1:
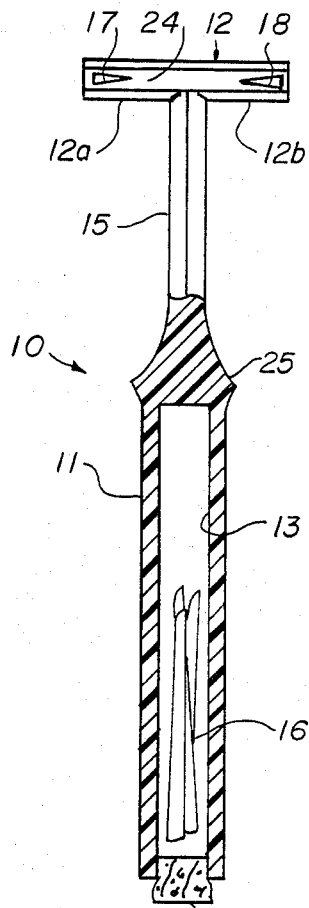
FIG. 1 is a front view in elevation, shown partly in section, of a toothpick holder according to the invention.
Figures 2, 3:
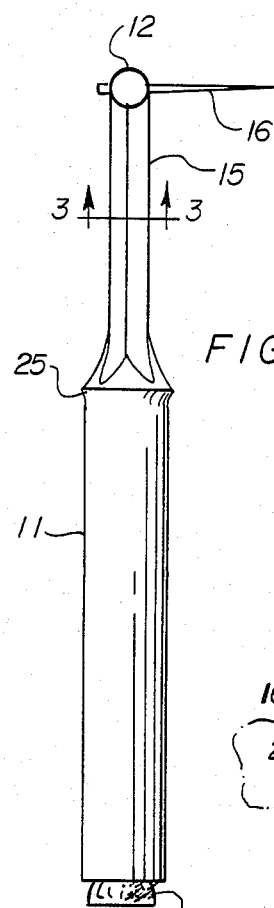
FIG. 2 is a side view in elevation of the toothpick holder of FIG. 1.
FIG. 3 is a transverse sectional view taken along line 3—3 in FIG. 2.
Figure 7:
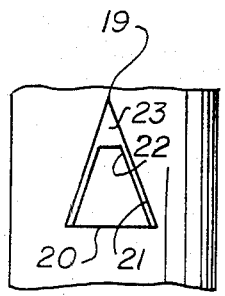
FIG. 7 is a fragmentary view in elevation, taken along line 7—7 in FIG. 6.

Referring more specifically to the drawings, a holder in accordance with the invention is indicated generally at 10 and comprises an elongate handle 11 having a cross-piece 12 at one end. A major portion of the length of the handle is hollow at 13, with the hollow end of the handle being open through the end opposite the cross-piece 12, and closed with any suitable means, such as cork 14. That part of the handle extending between the hollow end and the cross-piece comprises a stem 15, having a hexagonal cross section in the embodiment shown. The hollow handle end may be used for storage of toothpicks or the like 16, if desired.

Figure 6:
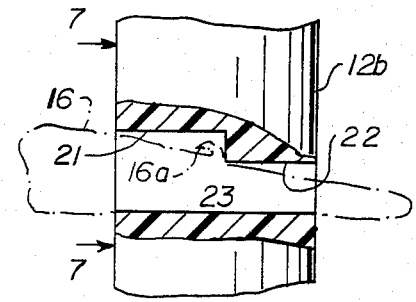
FIG. 6 is a slightly enlarged sectional view taken along line 6—6 in FIG. 5.
Figure 4:
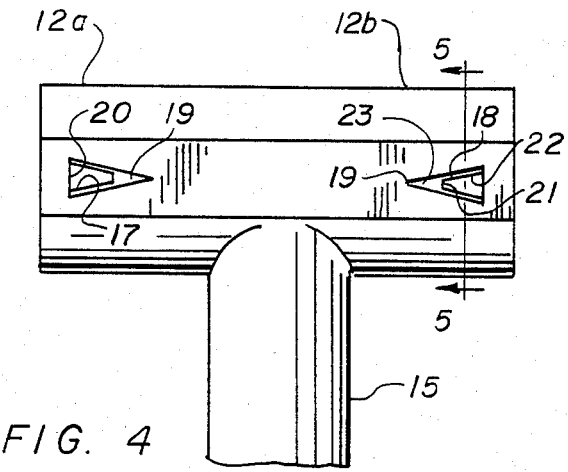
FIG. 4 is a greatly enlarged, fragmentary front elevational view of the cross-piece of the holder of FIG. 1.
Figure 5:
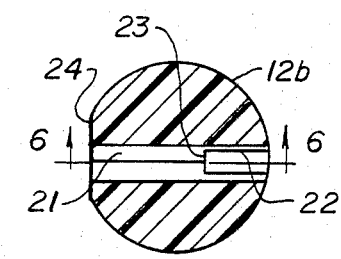
FIG. 5 is a transverse sectional view taken along line 5—5 of FIG. 4.
Figure 8:
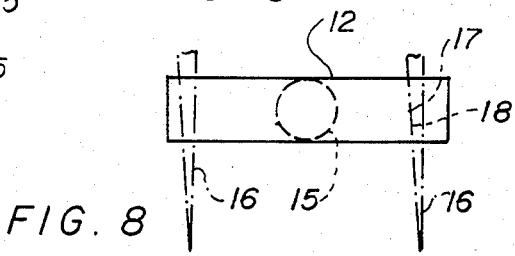
FIG. 8 is a slightly enlarged top or end view of the holder of FIGS. 1 through 7.

The ends 12a and 12b of the cross-piece projecting outwardly from the connection with the stem 15 have triangularly shaped openings 17 and 18 therethrough adjacent the free ends thereof, with the apex or narrow edge 19 of each opening being directed toward the inner ends of the arms and the base or flat ends 20 of the openings being disposed toward the free ends of the arms. The openings 17 and 18, as seen best in FIG. 6, are stepped between their ends, defining a larger opening 21 and a smaller opening 22, with a shoulder 23 formed at the juncture of the larger and smaller openings. Further, the relationship of the smaller and larger openings is the same at opposite ends of the cross-piece, so that a toothpick inserted through the openings is oriented as shown in full and dot-and-dash lines, respectively, in FIG. 8. As seen best in FIG. 6, when a toothpick 16 is inserted through one of the openings 17 and 18, a portion of the narrow edge of the toothpick engages the shoulder 23 and is shaved or rolled back at 16a, tending to wedge the toothpick in place.

In order to assist the user in inserting the toothpick through the proper opening, i.e. through the larger of the openings formed by the stepped configuration, a flat 24 is formed on the side of the arms in which the larger openings 21 are formed. The presence of the flat may be determined either by sight or touch. Moreover, in order to improve gripping of the handle, a shoulder or stop 25 may be formed between the hollow end and stem.

In use, a toothpick 16 is inserted into only one of the openings 17 or 18 at any given time. For instance, if the implement were to be used on the inner surfaces or interstices of the teeth on the left side of the mouth, a toothpick would be inserted into the opening 17 in the arm 12a as viewed in FIG. 1. This same toothpick orientation would also be used for the outer sides or interstices of the teeth on the right side of the mouth. Correspondingly, a toothpick would be inserted into the opening 18 in the other arm 12b when the surfaces of the teeth opposite those just described were desired to be cleaned.

The toothpick holder of the invention thus properly orients toothpicks having a wedge shape in cross-section for access to all interstices of the teeth from both the lingual and buccal sides of the teeth.

The holder may be manufactured from any suitable material, such as injection molded plastic, and it is particularly well adapted to use with toothpicks such as sold under the trademark STIM-U-DENT, by Johnson and Johnson.

In its present form, the holder has an overall length of about six inches and each arm 12a and 12b is about 7/16 inch long, with the bases of the openings 17 and 18 being spaced about 1/16 inch from the free outer end of the arm.

While the holder has been shown and described in detail, it is obvious that the invention is not to be limited to the exact form disclosed, and that changes in detail and construction may be made therein within the scope of the invention, without departing from the spirit thereof.

Having thus set forth and disclosed the nature of this invention what is claimed is:

1. A toothpick holder for selectively holding a toothpick in one of a plurality of orientations, comprising:
   an elongate handle having a cross-piece at one end;
   said cross-piece defining a pair of arms projecting laterally in opposite directions from the handle at substantially a right angle thereto and having free outer ends spaced from the handle; and
   each arm having a shaped opening extending transversely therethrough adjacent the free outer end for receiving and holding a toothpick inserted into and through the opening, whereby a toothpick inserted through the opening in one arm has an orientation essentially opposite the orientation of a toothpick inserted through the opening in the other arm, to facilitate access to the interstices between the teeth on opposite sides of the mouth.

2. A toothpick holder as defined in claim 1, wherein:
   the openings through each arm are stepped in longitudinal cross-sectional dimension, defining a larger opening and a smaller opening, forming a shoulder at the juncture between the larger and smaller openings, against which a toothpick engages when inserted through the opening, shaving a part of the toothpick back, tending to wedge the toothpick in place.

3. A toothpick holder as defined in claim 2, wherein:
   the openings through the arms are triangularly shaped in transverse cross-section, having a flat or base side toward the free outer end of each arm and a point or apex toward the handle.

4. A toothpick holder as defined in claim 3, wherein:
   the handle is hollow.

5. A toothpick holder as defined in claim 4, wherein:
   a flat is formed on one side of the cross-piece to enable identification of the side of each arm in which the larger of the openings is located.

* * * * *